United States Patent [19]
Widen

[11] Patent Number: 5,927,981
[45] Date of Patent: Jul. 27, 1999

[54] METHOD AND APPARATUS FOR BLEACHING TEETH

[76] Inventor: Randy Widen, 284 Elkins La., Lusby, Md. 20657

[21] Appl. No.: 09/026,692

[22] Filed: Feb. 20, 1998

[51] Int. Cl.$^6$ ........................................................ A61C 5/00
[52] U.S. Cl. .............................. 433/215; 433/32; 604/291
[58] Field of Search .............................. 433/32, 215, 216; 601/162; 604/113, 291

[56] References Cited

U.S. PATENT DOCUMENTS

| | | | |
|---|---|---|---|
| 173,795 | 2/1876 | Jordan | 433/32 |
| 1,209,599 | 12/1916 | Le Fevre | 433/80 |
| 1,267,761 | 5/1918 | Goodfellow | 604/113 |
| 2,200,008 | 5/1940 | Nowak | 604/291 |
| 3,749,092 | 7/1973 | Williams | 604/291 |
| 4,292,971 | 10/1981 | Smit et al. | 604/291 |
| 4,793,807 | 12/1988 | Friedmar et al. | 433/80 |
| 4,952,143 | 8/1990 | Becker et al. | 433/32 |
| 4,983,381 | 1/1991 | Zaragoza | 424/53 |
| 5,032,178 | 7/1991 | Cornell | 433/215 |
| 5,240,415 | 8/1993 | Haynie | 433/216 |
| 5,376,006 | 12/1994 | Fischer | 433/215 |

FOREIGN PATENT DOCUMENTS 2 645 734 A1   10/1980   France .

Primary Examiner—Ralph A. Lewis
Attorney, Agent, or Firm—Venable; Norman N. Kunitz

[57] ABSTRACT

A method and apparatus for bleaching teeth. The method involves heating a dental bleaching solution capable of yielding a bleaching vapor having a concentrated peroxide molecule content when heated until the bleaching vapor is obtained, and thereafter applying the bleaching vapor to a surface of at least one tooth in order to bleach the tooth. The apparatus includes a housing defining a chamber to be partially filled with a bleaching solution, the bleaching solution being capable of yielding a bleaching vapor having a concentrated peroxide content when heated. The apparatus further includes a heating device for heating the bleaching solution partially filling the chamber for generating the bleaching vapor within the chamber in pressurized form; a delivery device connected to the housing for delivering the pressurized bleaching vapor from the chamber to a surface of at least one tooth to be bleached; and a control device operatively associated with the chamber and the delivery device for regulating a delivery of the bleaching vapor to the surface of the tooth.

18 Claims, 1 Drawing Sheet

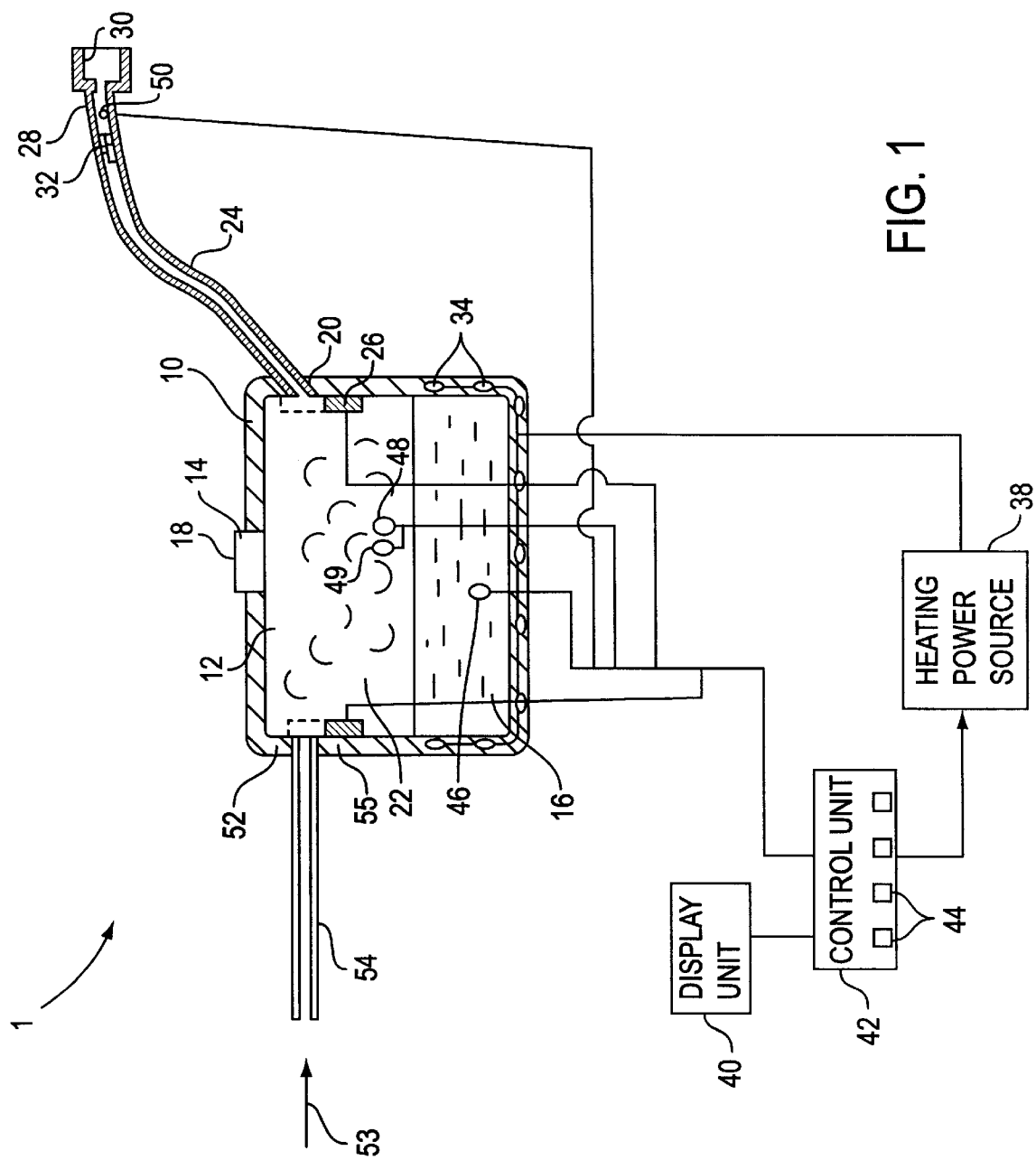

METHOD AND APPARATUS FOR BLEACHING TEETH

FIELD OF THE INVENTION

The invention relates to a method and an apparatus for bleaching teeth, and, in particular, to a method and apparatus which involve the heating of a bleaching solution for generating a bleaching vapor.

BACKGROUND OF THE INVENTION

The necessity of bleaching or whitening teeth arises in many instances, for example, where teeth have undergone root canal therapy and have thus become darkened, when the teeth have been traumatized by an accident, or when a gradual discoloring of the teeth has occurred due either to aging or to staining caused by certain foods such as coffee or beets. Teeth may be bleached even where the patient simply desires whiter looking teeth for aesthetic purposes.

It is known from the prior art to deliver a peroxide bleaching solution, such as a solution known in the dental trade as "superoxol," to the surface of teeth for bleaching the same. Superoxol is a peroxide solution and is additionally necessarily activated by the application of heat. The prior art discloses the activation of superoxol by applying heat to the very surface of the patient's teeth. For example, according to a known method of the prior art, a concentrated solution of peroxide is applied to the tooth surface, and, thereafter, a beam of optical energy is focused onto the tooth structure in order to additionally activate the peroxide.

In U.S. Pat. No. 4,952,143 to Becker et al., a dental bleaching instrument is disclosed where a peroxide solution is applied to either an individual tooth or multiple teeth and, in order to achieve the desired bleaching effect, heat is applied directly to the bleaching solution present on the teeth.

French Publication No. 2 645 734 to Ardiot et al pertains to a dental treatment unit for whitening teeth with a liquid agent such as hydrogen peroxide. The unit consists of a pump, a molded mouthpiece which covers the gums and palate while leaving a space exposing the teeth to be treated, a temperature sensor and a UV radiation source. The mouthpiece has a jet directing the liquid agent to the teeth. The UV radiation source accelerates the bleaching process by directing UV rays to the mouthpiece in order to activate the liquid agent present therein.

In U.S. Pat. No. 4,983,381 to Zaragoza, a thermocube or thermo-containing plate including a thermic heating unit is placed in a capsule or circular surface thereof. The thermocube or thermo-containing plate cover the teeth and are thereafter heated to activate a whitening agent for whitening the teeth. Here again, temperature is applied directly to the teeth.

U.S. Pat. No. 4,793,807 to Friedman et al concerns a delivery system for delivering a liquid heated to a predetermined temperature to the oral cavity of a patient. The liquid in question is not a bleaching agent, but a chemical solution which softens dental caries and thus aids in their removal.

The bleaching methods and apparatuses of the prior art have the disadvantage of yielding peroxide molecules which are not released until after the liquid bleaching solution has been delivered to the surface of the teeth. Because of the above, the bleaching capacity of the peroxide molecules is decreased, since the molecules have to overcome the surface tension of the bleaching solution liquid present on the surface of a tooth to be bleached in order to reach that surface and bleach the same.

In addition, the prior art necessarily requires the application of heat, sometimes using ultraviolet rays, directly to the oral cavity of the patient. With regard to the above, the prior art is limited, in the sense that any variation in the temperature of the bleaching solution, or any monitoring and/or regulation of that temperature, necessarily occurs directly on the surface of the tooth to be bleached. Thus, the prior art does not allow a monitoring/regulation of the temperature of the bleaching molecules for optimum bleaching before the peroxide reaches the tooth surface. Moreover, it is widely known, as shown by numerous studies, that ultraviolet rays have a negative effect upon both dentists and dental technicians working proximal to such rays, and the patient whose teeth are being treated. It is not clear whether the long term effects of exposure to ultraviolet rays have been fully appreciated.

To the extent that the prior art involves activation of a bleaching solution directly on the surface of a tooth to be bleached, it furthermore does not permit the delivery of a bleaching vapor in the form of a pressurized jet or stream to the tooth to be bleached. Since the use of a pressurized jet or stream increases the bleaching capacity of the vapor by allowing the same to more easily enter the enamel tubules, the prior art disadvantageously involves a bleaching process which is relatively slow and painstaking for both the patient and the dental practitioner.

It is an object of the invention to provide a method and apparatus for bleaching teeth where a bleaching vapor containing concentrated oxygen is delivered to the surface of a tooth to be bleached. According to the above object, the peroxide molecules may readily enter the enamel tubules of the tooth for bleaching the same without having to overcome the surface tension of a bleaching solution present on the tooth surface.

It is yet another object of the invention to provide a method and apparatus for bleaching teeth of the above type where a temperature of the bleaching vapor can be regulated before the vapor reaches the surface of the tooth to be bleached for maintaining an optimum temperature range of the bleaching vapor.

It is a further object of the invention to provide a method and apparatus for bleaching teeth where the use of ultraviolet rays is obviated.

It is yet a further object of the invention to provide a method and apparatus for bleaching teeth where the bleaching vapor can be delivered to the surface of the tooth to be bleached in the form of a pressurized jet or stream of bleaching vapor.

SUMMARY OF THE INVENTION

These objects and others to become apparent as the specification progresses are accomplished by the invention, according to which a method and an apparatus for bleaching teeth are provided as set forth below.

The method of the present invention involves heating a dental bleaching solution capable of yielding a bleaching vapor having a concentrated peroxide molecule content when heated, until the bleaching vapor is obtained, and thereafter applying the bleaching vapor directly to a surface of at least one tooth in order to bleach the tooth.

According to one embodiment of the invention, the bleaching solution is heated in a semi-closed chamber such that the resulting bleaching vapor is created within the chamber. The bleaching vapor is then delivered in the form of a jet or stream to the surface of the tooth to be bleached. In order to increase the pressure of the jet or stream of bleaching vapor being delivered to the surface of the tooth, pressurized air may be delivered to the chamber from any suitable source. Preferably, a release of pressurized bleaching vapor from the chamber into an applicator tube connected to the chamber is effected according to the invention after the bleaching vapor has reached a predetermined escapement pressure inside the chamber somewhat greater than atmospheric. Moreover, the jet or stream of pressurized vapor may be held in contact with the surface of the tooth to be bleached with a tooth conforming seal attached to an end of the applicator tube until a desired degree of bleaching is effected. The seal may be slid or moved from one increment to another increment of the surface of the tooth for bleaching the surface of the tooth increment by increment. In addition, the bleaching solution may be heated such that a partial escapement pressure at a discharge orifice of the applicator for discharging the jet or stream of pressurized vapor is about 25 psi.

According to a preferred embodiment of the present invention, the dental bleaching solution is heated electrically.

According to another embodiment of the invention, the surface of the tooth to be bleached is etched with ortho phosphoric acid before the bleaching vapor is delivered thereto.

Preferably, the bleaching vapor is heated to a temperature of about 140° F. at escapement from the discharge orifice.

The apparatus according to the invention includes a housing defining a chamber to be partially filled with a bleaching solution, the bleaching solution being capable of yielding a bleaching vapor having a concentrated peroxide molecule content when heated. The apparatus further includes a heating means operatively associated with the chamber for heating the bleaching solution in the chamber to generate bleaching vapor and partially filling the chamber with bleaching vapor in pressurized form; a delivery means connected to the housing for delivering the pressurized bleaching vapor from the chamber to a surface of at least one tooth to be bleached; and control means operatively associated with the chamber and the delivery means for regulating a delivery of the bleaching vapor to the surface of the tooth.

Preferably, the heating means comprise electrical heating coils operatively connected to the housing.

According to one embodiment of the invention, the housing has a vapor escapement outlet therein which allows the bleaching vapor to escape therethrough from the chamber to the delivery means. The delivery means includes a flexible applicator tube having a first end and a second end, with the first end of the applicator tube being connected to the housing at the vapor escapement outlet such that the applicator tube is in flow communication with the chamber through the vapor escapement outlet, and with the applicator tube further including an applicator orifice at its second end for allowing the bleaching vapor to be discharged to the surface of the tooth. In addition, the delivery means includes a tooth conforming seal, preferably made of rubber, connected to the second end of the applicator tube at the applicator orifice. The seal is adapted to hold the bleaching vapor discharged from the applicator orifice at the surface of the tooth for bleaching the tooth. Preferably, the control means comprises an outlet closure means adapted to be actuated into a closed position where the outlet closure means sealingly closes the vapor escapement outlet, and an open position where the outlet closure means is disposed such that bleaching vapor is allowed to escape through the outlet closure means into the delivery means. The control means may further comprise means for actuating the outlet closure means into its open position when a pressure of the bleaching vapor inside the chamber has reached a predetermined escapement pressure.

According to another feature of the invention, the housing an air inlet therein, and an air supply line is connected to the housing at the air inlet for supplying pressurized air to the chamber through the air inlet for thereby increasing the pressure of the bleaching vapor being delivered to the surface of the tooth.

According to yet another feature of the invention, the control means comprises temperature sensor for sensing the temperature of the bleaching solution disposed inside the chamber, and a control unit responsive to the temperature of the bleaching solution sensed by the temperature sensor for regulating the heating activity of the heating means.

Preferably, the delivery means includes an orifice adapted to be disposed adjacent the surface of the tooth for allowing the bleaching vapor to be discharged thereto. The control means may comprise both a pressure sensor for sensing a partial pressure of vapor at the orifice, and a control unit responsive to the partial pressure of vapor at the orifice sensed by the pressure sensor for regulating the heating activity of the heating means.

According to further featured of the invention, the housing is made from at least one of metal and glass.

BRIEF DESCRIPTION OF THE DRAWINGS

Further features and details of the present invention will become evident from the description below of an embodiment thereof that is illustrated in the sole FIGURE, which is a schematic cross section of the dental bleaching device according to the invention.

DETAILED DESCRIPTION OF THE INVENTION

Referring now to the drawing, the sole FIGURE shows a schematic, simplified version of the dental bleaching device 1 according to the invention. Dental bleaching device 1 comprises a housing 10 made of a material not corroded by conventional dental bleaching solutions, such as glass or metal. Housing 10 defines a hollow chamber 12 therein, which is accessible via an opening 14 formed in one wall of housing 10. Opening 14 allows the introduction into hollow chamber 12 of a dental bleaching solution 16, such as superoxol, or any other conventional dental bleaching solution which when heated yields a bleaching vapor having a concentrated peroxide molecule content, that is, a bleaching vapor 22 having an increased partial pressure content. Opening 14 is closeable by means of a suitable cap 18, which sealingly engages the opening 14 for closing the same in an air-tight manner.

Housing 10 further includes a vapor escapement outlet 20 through which dental bleaching vapor 22 formed within chamber 12 can escape into a flexible bleaching agent applicator tube 24 connected to the housing 10 in a conventional manner. A conventional outlet closure 26 for outlet 20 is provided with the closure 26 being controllably actuable into either an open position, shown in solid lines in the FIGURE, where vapor can escape from outlet 20 into applicator tube 24, or a normal closed position, shown in dashed lines in the FIGURE, where vapor is prevented from escaping chamber 12 and entering applicator tube 24. It is to be understood however that other arrangements for selectively preventing a stream vapor from flowing through tube 24 may be utilized, e.g., a valve at the other end of the tube 24 or a clip on the tube 24. Applicator tube 24 is effective for supplying the bleaching vapor to an applicator orifice 28. A tooth conforming rubber seal 30 of conventional design is disposed at an extremity of applicator tube 24 adjacent orifice 28 for receiving a stream 32 of bleaching vapor from orifice 28 and for holding the bleaching vapor on a tooth to be bleached.

The housing 10 is provided with a heating arrangement for heating the dental bleaching solution 16 present within hollow chamber 12. In the embodiment shown in the FIGURE, the heating arrangement includes conventional electrical heating coils 34 mounted on or disposed in the housing 12 and connected to a controlled electrical power source 38 of conventional design. Additionally provided are a display unit 40, and an associated control unit 42, having suitable control keys 44 for mounting and/or effecting a variety of control functions with respect to the illustrated device as will be described further below. The power source 38 may supply a voltage of 110 V to the circuit. Two conventional temperature sensor probes 46 and 48 are provided as shown for sensing the temperature of the bleaching solution 16 and of the bleaching vapor 22, respectively. A conventional pressure sensor probe 49 is also provided for sensing the pressure of the bleaching vapor inside the chamber 12. Moreover, a conventional pressure sensor probe 50 is provided for sensing the partial pressure of the vapor stream 32 at orifice 28.

Hollow chamber 12 is preferably accessible to a supply of air under pressure via an air inlet 52 provided in housing 10. Air under pressure 53 supplied from a conventional source of pressurized air (not shown) is conducted to air inlet 52 by an air supply line 54. Similar to outlet 20, inlet 52 includes a conventional inlet closure arrangement 55 which is to be either in an open position, shown in solid lines in the FIGURE, where air under pressure can enter hollow chamber 12 through inlet 52, and a normal closed position, shown in dashed lines in the FIGURE, where air is prevented from entering the hollow chamber 12.

In operation, cap 18 is disengaged from opening 14, and bleaching solution 16 is introduced into hollow chamber 12 via opening 14 in a suitable amount, depending among other things on the capacity of hollow chamber 12 and also on the bleaching intensity desired and the number of teeth to be bleached. It must be kept in mind that chamber 12 should never be completely filled with bleaching solution so as to allow room for the formation of bleaching vapor therein. Preferably, bleaching solution 16 consists of superoxol, containing about 30%–50% hydrogen peroxide. After hollow chamber 12 is filled to the desired extent, opening 14 is sealingly closed in an air tight manner by cap 18 as shown.

Heating of bleaching solution 16 is effected by heating coils 34, which are activated by power source 38 by means of suitable controls, such as a general hand-operated on/off key control, as depicted in the drawing by key controls 44. Thus, actuation of an on/off key control, or switch, closes or completes the electrical circuit power in a conventional manner in order to supply power to coils 34 for heating the bleaching solution 16. When heated to the required temperature, bleaching solution 16 is vaporized to yield a vapor having a concentrated peroxide molecule partial pressure content. As bleaching solution 16 is heated within hollow chamber 12, the resulting vapor 22, which is preferably combined with additive air as explained below, causes the pressure to increase within the hollow chamber 12 when the pressure has reached a pressure sufficiently high to produce a desired flow, i.e., a slightly higher than atmospheric rate, then the closure 26 is moved into its open position to reach an escapement pressure. The temperature of bleaching solution 16, and both the temperature and pressure of bleaching vapor 22 are sensed by respective ones of temperature/pressure sensor probes 46, 48 and 49 as set forth above.

Two modes of actuation of outlet closure 26 are contemplated according to the invention. According to the first mode, the sensed temperature and pressure values are transmitted to a conventional display unit 40, which in turn displays those values to the operator of the bleaching device. Once display unit 40 indicates the pressure of bleaching vapor 22 sensed by pressure sensor probe 49 as having reached a desired pressure, the operator actuates a suitable one of key controls 44 to effect an activation of outlet closure means 26 in order to move the outlet closure means into its open position. According to the second mode, the sensed temperature and pressure values are transmitted to control unit 42. Once the control unit senses that the pressure of bleaching vapor has reached the desired pressure, it automatically effects an activation of outlet closure 26 in order to move the outlet closure into an open position. It is apparent from the above description that the first and second modes correspond to manual and computer controlled actuation of outlet closure 26, respectively. The interrelationship between the sensor probes, the display unit and the control unit including the key controls can be effected as is customary in the art in order to achieve the desired temperature and pressure evaluation and actuation of the outlet closure 26.

Subsequent to the actuation of outlet closure 26 into its open position, a stream of bleaching vapor 32 begins flowing along applicator tube 24 toward orifice 28 of rubber seal 30, and escapes from orifice 28 as a stream of bleaching vapor. When superoxol is used, the partial pressure of peroxide molecules at applicator orifice 28 should be about 25 psi. The temperatures sensed by temperature sensor probes 46 and 48, the pressure sensed by sensor probe 49, and the oxygen partial pressure sensed by pressure sensor probe 50 at orifice 28 are transmitted to control unit 42. Control unit 42 in turn regulates the supply of power to electrical coils 34 as a function of the sensed temperature and pressure values transmitted thereto. Thus, in the shown embodiment, if the temperature of the bleaching vapor inside hollow chamber 12 deviates from the required temperature of about 140° F., or if the oxygen partial pressure of vapor stream 32 at orifice 28 deviates from the desired pressure of about 25 psi, control unit 42 regulates the power supplied by the power source 38 to supply either more or less power to the heating coils 34 in order to advantageously increase or decrease the heating activity of coils 34. According to a further embodiment of the invention, the regulation of power as a function of sensed temperature and pressure values can be effected manually, by means of key controls 44, by observing the sensed values displayed on display unit 40, much in the same manner as explained with respect to the manual control of outlet closure means 26 above.

Advantageously, the force of the stream of bleaching vapor escaping from orifice 28 can be increased by pumping pressurized air into hollow chamber 12. In order to accomplish the above, inlet closure 55 is actuated to move into its open position. In this manner, air inlet 52 allows the entry of pressurized air 53 into hollow chamber 12, which in turn increases the pressure within the chamber. An increase of the pressure within hollow chamber 12 manifests itself as increased pressure of the stream of bleaching vapor escaping from orifice 28. In this manner, bleaching efficiency of the device is increased.

The stream of bleaching vapor escaping from orifice 28, because of its concentrated peroxide content, has the ability to bleach teeth. In a conventional manner, the surface of the tooth to be bleached is preferably etched with ortho phosphoric acid before being exposed to the bleaching vapor. Thus, according to the invention, the rubber seal 30 is positioned upon a tooth whose surface has been etched as mentioned above, and concentrated peroxide molecules are as a result delivered to the tooth surface to bleach the same. Factors determining the bleaching extent of the tooth include the pressure of the stream of bleaching vapor at orifice 28 and the amount of time the rubber seal 30 is held in one position.

According to a preferred embodiment of the invention, the rubber seal is in the form of a hand held wand as generally shown, which is smaller than the side of a tooth surface. Thus, as each increment of the tooth surface is bleached, the wand is slid into an alternate tooth surface increment in order to continue bleaching the surface of the tooth.

The foregoing is a complete description of the present invention. It will be understood that the above description of the present invention is susceptible to various modifications, changes and adaptations, and the same are intended to be comprehended within the meaning and range of equivalent of the appended claims.

What is claimed is:

1. A method for bleaching teeth comprising the steps of:
   providing a dental bleaching solution adapted to yield a bleaching vapor having a concentrated peroxide molecule content when heated;
   heating the dental bleaching solution until the bleaching vapor is obtained;
   thereafter conveying the bleaching vapor to a tooth to be bleached and applying the bleaching vapor to a surface of at least one tooth in order to bleach the tooth.

2. The method according to claim 1, wherein:
   the step of conveying and heating includes the step of heating the bleaching solution in a closed chamber such that the bleaching vapor is pressurized within the chamber; and
   the step of applying includes the step of delivering the bleaching vapor in a stream of pressurized bleaching vapor to the surface of the tooth.

3. The method according to claim 2, further including the step of delivering pressurized air into the chamber for increasing a pressure of the stream of pressurized bleaching vapor being delivered to the surface of the tooth.

4. The method according to claim 2, wherein the step of delivering includes the step of effecting a release of the pressurized bleaching vapor from the chamber into an applicator tube connected to the chamber after the bleaching vapor has reached a predetermined escapement pressure inside the chamber.

5. The method according to claim 4, wherein; a tooth conforming seal is attached to a free end of the applicator tube; and the step of delivering further includes the step of holding the tooth conforming seal in contact with the surface of the tooth to direct the stream of pressurized bleaching vapor onto the surface of the tooth until a desired degree of bleaching is effected.

6. The method according to claim 5, wherein the step of delivering further includes the step of moving the seal from one increment to another increment of the surface of the tooth for bleaching the surface of the tooth increment by increment.

7. The method according to claim 4, wherein the step of heating includes the step of heating the bleaching solution such that a partial pressure of about 25–45 psi is present at a discharge orifice of the applicator tube for discharging the stream of pressurized bleaching vapor.

8. The method according to claim 1, wherein the step of heating includes the step of electrically heating the dental bleaching solution.

9. The method according to claim 1, further including the step of etching the surface of the tooth with ortho phosphoric acid before the step of applying.

10. The method according to claim 1, wherein the step of heating includes the step of heating the bleaching solution to a temperature of about 140° F.

11. An apparatus for bleaching teeth according to the method of claim 1, comprising:
    a housing defining a chamber adapted to be partially filled with a bleaching solution capable of yielding a bleaching vapor having a concentrated peroxide molecule
    a housing defining a chamber adapted to be partially filled with a bleaching solution capable of yielding a bleaching vapor having a concentrated peroxide molecule content when heated;
    a heating means operatively associated with the chamber for heating the bleaching solution partially filling the chamber for generating the bleaching vapor within the chamber in pressurized form;
    a delivery means connected to the housing for delivering the pressurized bleaching vapor from the chamber to a surface of at least one tooth to be bleached; and
    control means operatively associated with the chamber and the delivery means for regulating a delivery of the bleaching vapor he surface of the tooth; and, wherein:
      the housing defines a vapor escapement outlet therein, the vapor escapement outlet allowing the bleaching vapor to escape therethrough from the chamber to the delivery means; and the delivery means includes:
        a flexible applicator tube having a first end and a second end, the first end of the applicator tube being connected to the housing at the vapor escapement outlet such that the applicator tube is in flow communication with the chamber through the vapor escapement outlet, the applicator tube further including an applicator orifice at its second end for allowing the bleaching vapor to be discharged to the surface of the tooth; and
        a tooth conforming seal connected to the second end of the applicator tube at the applicator orifice and adapted to hold the bleaching vapor discharged from the applicator orifice at the surface of the tooth for bleaching the tooth.

12. The apparatus according to claim 11, wherein the heating means comprise electrical heating coils operatively connected to the housing.

13. The apparatus according to claim 11, wherein the control means comprises an outlet closure means adapted to be actuated into a closed position where the outlet closure means sealingly closes the vapor escapement outlet, and an open position where the outlet closure means allows bleaching vapor to escape the chamber through the vapor escapement outlet.

14. The apparatus according to claim 13, wherein the control means further comprises means for actuating the outlet closure means into its open position when a pressure of the bleaching vapor inside the chamber has reached a predetermined pressure.

15. An apparatus for bleaching teeth according to the method of claim 1, comprising:

a housing defining a chamber adapted to be partially filled with a bleaching solution capable of yielding a bleaching vapor having a concentrated peroxide molecule content when heated;

a heating means operatively associated with the chamber for heating the bleaching solution partially filling the chamber for generating the bleaching vapor within the chamber in pressurized form;

a delivery means connected to the housing for delivering the pressurized bleaching vapor from the chamber to a surface of at least one tooth to be bleached; and control means operatively associated with the chamber and the delivery means for regulating a delivery of the bleaching vapor he surface of the tooth; and, wherein the housing defines an air inlet therein, the apparatus further including an air supply line connected to the housing at the air inlet for supplying pressurized air to the chamber through the air inlet for increasing a pressure of the bleaching vapor being delivered to the surface of the tooth.

16. An apparatus for bleaching teeth according to the method of claim 1, comprising:

a housing defining a chamber adapted to be partially filled with a bleaching solution capable of yielding a bleaching vapor having a concentrated peroxide molecule content when heated;

a heating means operatively associated with the chamber for heating the bleaching solution partially filling the chamber for generating the bleaching vapor within the chamber in pressurized form;

a delivery means connected to the housing for delivering the pressurized bleaching vapor from the chamber to a surface of at least one tooth to be bleached; and control means operatively associated with the chamber and the delivery means for regulating a delivery of the bleaching vapor he surface of the tooth; and, wherein the control means comprises:

temperature sensor means for sensing a temperature of the bleaching solution inside the chamber; and a control unit responsive to the temperature of the bleaching solution sensed by the temperature sensor means for regulating a heating activity of the heating means.

17. An apparatus for bleaching teeth according to the method of claim 1, comprising:

a housing defining a chamber adapted to be partially filled with a bleaching solution capable of yielding a bleaching vapor having a concentrated peroxide molecule content when heated;

a heating means operatively associated with the chamber for heating the bleaching solution partially filling the chamber for generating the bleaching vapor within the chamber in pressurized form;

a delivery means connected to the housing for delivering the pressurized bleaching vapor from the chamber to a surface of at least one tooth to be bleached; and control means operatively associated with the chamber and the delivery means for regulating a delivery of the bleaching vapor he surface of the tooth; and, wherein:

the delivery means includes an orifice adapted to be disposed adjacent the surface of the tooth for allowing the bleaching vapor to be discharged to the surface of the tooth; and the control means comprises:

pressure sensor means for sensing a partial pressure of flow at the orifice; and a control unit responsive to the partial pressure of flow at the orifice sensed by the pressure sensor means for regulating a heating activity of the heating means.

18. An apparatus for bleaching teeth according to the method of claim 1, comprising:

a housing defining a chamber adapted to be partially filled with a bleaching solution capable of yielding a bleaching vapor having a concentrated peroxide molecule content when heated, with the housing being made from at least one of metal and glass;

a heating means operatively associated with the chamber for heating the bleaching solution partially filling the chamber for generating the bleaching vapor within the chamber in pressurized form;

a delivery means connected to the housing for delivering the pressurized bleaching vapor from the chamber to a surface of at least one tooth to be bleached; and control means operatively associated with the chamber and the delivery means for regulating a delivery of the bleaching vapor to the surface of the tooth.

* * * * *